United States Patent
Wood

(10) Patent No.: US 6,776,162 B2
(45) Date of Patent: Aug. 17, 2004

(54) VENTILATION INTERFACE FOR SLEEP APNEA THERAPY

(75) Inventor: Thomas J. Wood, Waycross, GA (US)

(73) Assignee: Innomed Technologies, Inc., Boca Raton, FL (US)

( * ) Notice: Subject to any disclaimer, the term of this patent is extended or adjusted under 35 U.S.C. 154(b) by 0 days.

(21) Appl. No.: 10/096,795

(22) Filed: Mar. 14, 2002

(65) Prior Publication Data

US 2002/0092527 A1 Jul. 18, 2002

Related U.S. Application Data

(63) Continuation-in-part of application No. 10/044,925, filed on Jan. 15, 2002, now Pat. No. 6,595,215, which is a continuation-in-part of application No. 09/524,371, filed on Mar. 13, 2000, now Pat. No. 6,478,026.

(51) Int. Cl.[7] ............................................... A61M 15/08
(52) U.S. Cl. ............................... 128/207.18; 128/207.13
(58) Field of Search ....................... 128/200.24, 207.12, 128/207.13, 207.18, 203.29, 204.12, 205.24, 205.27, 205.29, 206.11, 206.15, 206.16, 206.17, 206.18; 600/529, 532, 538

(56) References Cited

U.S. PATENT DOCUMENTS

| | | | |
|---|---|---|---|
| 853,431 A | * 5/1907 | Allen | 128/207.18 |
| 1,125,542 A | * 1/1915 | Humphries | 128/207.18 |
| 3,513,844 A | 5/1970 | Smith | |
| 3,902,486 A | * 9/1975 | Guichard | 128/203.22 |
| 4,106,505 A | 8/1978 | Salter et al. | |
| 4,156,426 A | * 5/1979 | Gold | 128/204.18 |
| D262,322 S | 12/1981 | Mizerak | |
| 4,535,767 A | * 8/1985 | Tiep et al. | 128/207.18 |
| 4,660,555 A | * 4/1987 | Payton | 128/207.18 |
| 4,774,946 A | 10/1988 | Ackerman et al. | |

(List continued on next page.)

Primary Examiner—Teena Mitchell
(74) Attorney, Agent, or Firm—Keady, Olds & Maier, PLLC

(57) ABSTRACT

The ventilation interface for sleep apnea therapy interfaces a ventilation device to the patient's airways. The ventilation interface includes a pair of nasal inserts made from flexible, resilient silicone which are oval shaped in cross-section and slightly tapered from a base proximal the ventilation supply to the distal tip end. A bead flange is disposed about the exterior of each insert at the distal end of the insert. In one embodiment, a valve is disposed between the nasal inserts and a source of positive airway pressure, the valve having a rim with a one-way diaphragm pivotally attached to the valve body with an inflatable bladder depending from the rim which seals against an exit port during inspiration and deflates to uncover the exit port on expiration. Another embodiment has nasal inserts without positive airway pressure but with a removable filter in the inserts for filtering inspired air.

13 Claims, 12 Drawing Sheets

U.S. PATENT DOCUMENTS

| | | | | |
|---|---|---|---|---|
| 4,782,832 A | | 11/1988 | Trimble et al. | |
| 4,915,104 A | | 4/1990 | Marcy | |
| 4,915,105 A | | 4/1990 | Lee | |
| 5,005,571 A | * | 4/1991 | Dietz | 128/205.25 |
| 5,025,805 A | | 6/1991 | Nutter | |
| 5,046,491 A | | 9/1991 | Derrick | |
| 5,099,836 A | * | 3/1992 | Rowland et al. | 128/204.23 |
| 5,113,857 A | * | 5/1992 | Dickerman et al. | 128/207.18 |
| 5,137,017 A | * | 8/1992 | Salter | 128/207.18 |
| D333,015 S | | 2/1993 | Farmer et al. | |
| 5,269,296 A | | 12/1993 | Landis | |
| 5,335,654 A | | 8/1994 | Rapoport | |
| 5,335,659 A | | 8/1994 | Pologe | |
| 5,477,852 A | | 12/1995 | Landis et al. | |
| 5,509,409 A | | 4/1996 | Weatherholt | |
| 5,533,506 A | | 7/1996 | Wood | |
| 5,535,739 A | | 7/1996 | Rapoport et al. | |
| 5,572,994 A | | 11/1996 | Smith | |
| 5,636,630 A | | 6/1997 | Miller et al. | |
| 5,682,881 A | | 11/1997 | Winthrop et al. | |
| 5,687,715 A | | 11/1997 | Landis et al. | |
| 5,704,916 A | | 1/1998 | Byrd | |
| 5,740,799 A | | 4/1998 | Nielsen | |
| 5,794,619 A | * | 8/1998 | Edelman et al. | 128/207.18 |
| 6,422,240 B1 | * | 7/2002 | Levitsky et al. | 128/207.18 |
| 6,439,234 B1 | * | 8/2002 | Curti et al. | 128/207.18 |
| 6,679,265 B2 | * | 1/2004 | Strickland et al. | 128/207.18 |
| 6,684,882 B1 | * | 2/2004 | Morine | 128/206.11 |

* cited by examiner

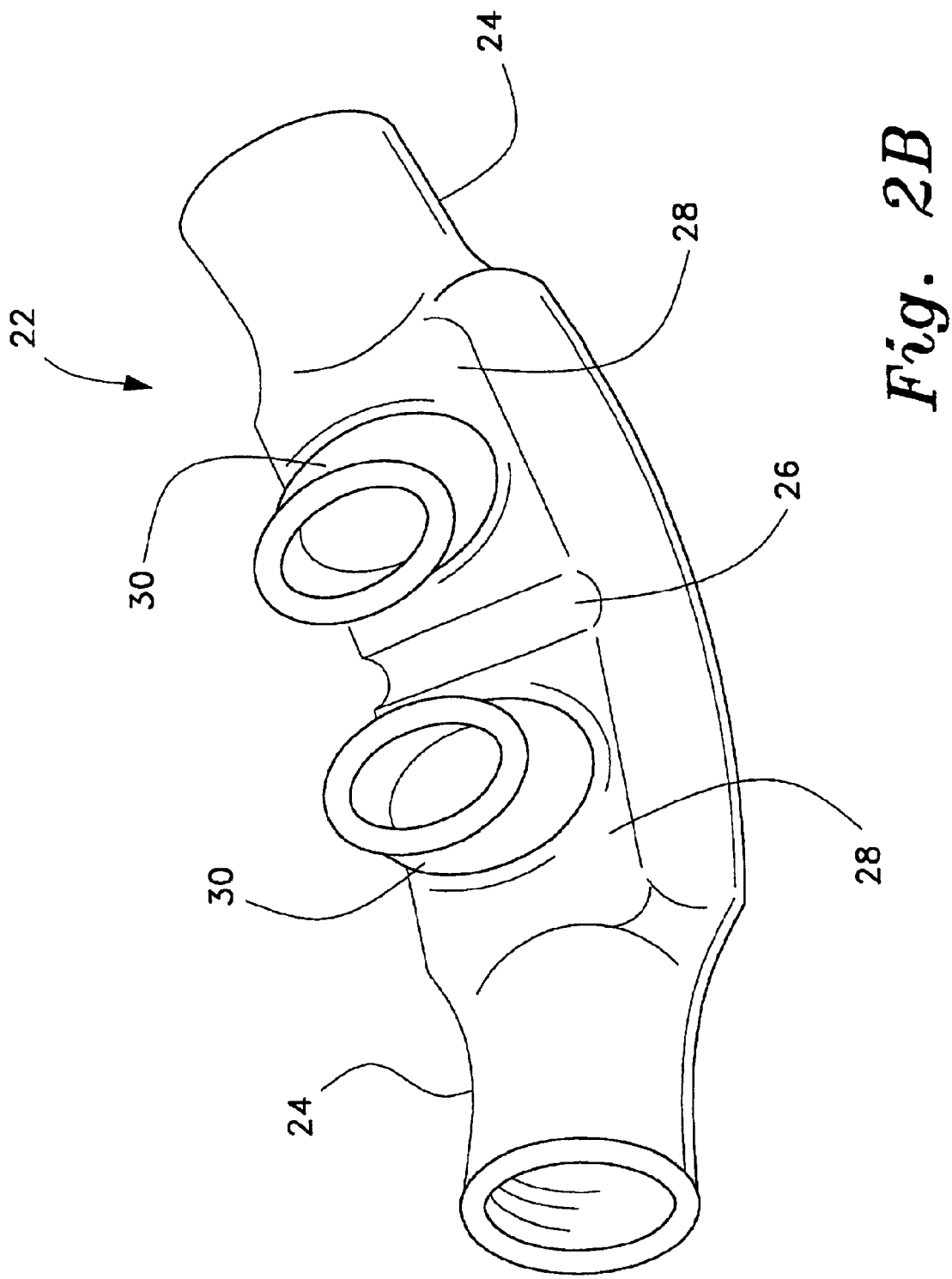

VENTILATION INTERFACE FOR SLEEP APNEA THERAPY

CROSS REFERENCE TO RELATED APPLICATIONS

This is a continuation-in-part of my prior application Ser. No. 10/044,925, filed Jan. 15, 2002 now U.S. Pat. No. 6,595,215, which is a continuation-in-part of my prior application Ser. No. 09/524,371, filed Mar. 13, 2000, U.S. Pat. No. 6,478,026.

BACKGROUND OF THE INVENTION

1. Field of the Invention

The present invention relates to ventilation devices, and particularly to a ventilation device having a nasal inserts which are inserted into the nostrils and seal against the nostrils without the aid of harnesses, head straps, adhesive tape or other external devices, and having exhalation ports designed to eliminate whistling noises, the ventilation interface having particular utility in various modes of therapy for obstructive sleep apnea. The invention may include a valve used in lieu of the exhalation ports, and may include nasal inserts used with filters for eliminating allergens and irritants from inhaled air but used without positive airway pressure.

2. Description of the Related Art

Sleep apnea is a potentially lethal affliction in which breathing stops recurrently during sleep. Sleep apnea may be of the obstructive type (sometimes known as the pickwickian syndrome) in which the upper airway is blocked in spite of airflow drive; the central type with decreased respiratory drive; or a mixed type. Breathing may cease for periods long enough to cause or to exacerbate cardiac conditions, and may be accompanied by swallowing of the tongue. Sleep apnea frequently results in fitful periods of both day and night sleeping with drowsiness and exhaustion, leaving the patient physically and mentally debilitated.

In recent years it has been found that various forms of positive airway pressure during sleep can be an effective form of therapy for the apnea sufferer. Ventilation can be applied in the form of Continuous Positive Airway Pressure (CPAP) in which a positive pressure is maintained in the airway throughout the respiratory cycle, Bilevel Positive Airway Pressure (BiPAP) in which positive pressure is maintained during inspiration but reduced during expiration, and Intermittent Mechanical Positive Pressure Ventilation in which pressure is applied when an episode of apnea is sensed. Positive airway pressure devices have traditionally employed either a face mask which only covers the patient's nose, or nasal pillows as the interface between the ventilation device and the patient's airway. However, there are problems with both of these interfaces.

The face mask requires a harness, headband, or other headgear to keep the mask in position, which many patient's find uncomfortable, particularly when sleeping. The face mask must seal the mask against the patient's face, and may cause irritation and facial sores, particularly if the patient moves his head while sleeping, causing the mask to rub against the skin. Face masks are also position dependent, and may leak if the mask changes position with movement of the patient's head. The face mask applies pressure to the sinus area of the face adjacent to the nose, causing the airways to narrow, thereby increasing the velocity of flow through the airway, but decreasing the pressure against the nasal mucosal walls. This strips moisture from the mucosal wall during inspiration, thereby causing drying and a burning sensation. These factors will often result in the patient's removal of the mask and discontinuance of positive airway pressure therapy.

Nasal pillows are pillowed style nasal seals which are pressed against the inferior portion of the nares to close the nostril openings. Nasal pillows require a headband or harness to maintain the pressure, resulting in the same patient discomfort noted with face masks. Nasal pillows have about a 0.25" internal diameter at the nasal entry port where the seal is made. Therefore, pressurized air must pass through a constricted port, increasing the velocity of airflow, with resultant drying and burning of the nasal airways. The narrowed interface diameter of the nasal pillows causes a pressure drop, which is directly proportional to the drop in the number of available air molecules within the closed system. It is the volume of air molecules at the area in the patient's throat where the apneic events appear that is needed to correct apnea. The narrower the airways or the internal diameter of the nasal interface, the lower the volume of air molecules that will be available and the greater the driving pressure that is required to meet the volume demand. An increase in driving pressure does not fully compensate for the loss in the number of air molecules available.

A further problem with existing ventilation devices is that the carbon dioxide bleed ports for venting exhaled gases are noisy on both nasal face masks and nasal pillows. The whistling noise that occurs while utilizing such devices can prove quite annoying to the patient, awakening the patient and causing the patient to discontinue use of the ventilation device.

A number of devices have been proposed which include a ventilation interface for supplying gases to be inhaled, for collecting exhaled gases, or for mounting sensors for measuring or monitoring respiratory function.

U.S. Pat. Nos. 5,335,654 and 5,535,739, issued on Aug. 9, 1994 to Rapoport and Jul. 16, 1996 to Rapoport et al., respectively, describe a CPAP system using a conventional nasal mask, the innovation comprising a flow sensor in the input line connected to a signal processor to determine the waveform of airflow, which is connected to a flow controller to adjust the pressure of airflow as required. U.S. Des. Pat. No. 333,015, issued Feb. 2, 1993 to Farmer et al. shows an ornamental design for a nasal mask. U.S. Des. Pat. No. 262,322, issued Dec. 15, 1981 to Mizerak, shows an ornamental design for a nasal cannula with a mouth mask.

U.S. Pat. No. 4,782,832, issued Nov. 8, 1988 to Trimble et al., discloses nasal pillows held in the patient's nose by a harness arrangement, the device having a plenum with two accordion or bellows shaped nipples for fitting against the nostril openings. U.S. Pat. Nos. 4,774,946, issued Oct. 4, 1988 to Ackerman et al., teaches a nasal and endotracheal tube apparatus for administering CPAP to infants, the nose tubes having a bulbous portion for seating in the nares of an infant and a headband with a Velcro® closure for supporting the cannula and supply tubes.

U.S. Pat. Nos. 5,269,296, issued to Landis on Dec. 14, 1993, and 5,477,852 and 5,687,715, issued to Landis et al. on Dec. 26, 1995, and Nov. 18, 1997, respectively, describe CPAP devices for the treatment of sleep apnea with relatively stiff or rigid nasal cannulae or prongs surrounded by inflatable cuffs to retain the cannulae in the nares, but which also may be supplemented by an inflatable head harness to position the cannulae and hold them in place, the two cannulae being joined by a conduit having vent holes to vent exhaled air. U.S. Pat. No. 5,533,506, issued Jul. 9, 1996 to the present inventor, discloses a nasal tube assembly in which the tubes are tapered, frustro-conical assemblies with a soft membrane over the distal tip and a washer at the base of the nasal tube to prevent the tubes from falling through a support bar connected to a harness, the nasal tubes forming a positive seal with the inside of the nostrils to prevent the escape of gases.

U.S. Pat. No. 5,682,881, issued Nov. 4, 1997 to Winthrop et al., shows a nasal cannula for CPAP therapy with cone shaped nasal prongs in which the cannula is secured to the patient's upper lip by adhesive tape strips. U.S. Pat. No. 4,915,105, issued Apr. 10, 1990 to Lee, teaches a miniature respiratory breather apparatus in which relatively stiff or rigid nasal tubes have elastomeric packings for sealing the tubes in the nares.

Several patents describe improvements to nasal cannulae, but without sealing the nose tubes against the nostrils to prevent leakage of gas, including: U.S. Pat. No. 3,513,844, issued May 26, 1970 to Smith (metal strip in cannula cross-tube to retain configuration matching patient's lip); U.S. Pat. No. 4,106,505, issued Aug. 15, 1978 to Salter et al. (cannula body with ends extending upward and rearward); U.S. Pat. No. 4,915,104, issued Apr. 10, 1990 to Marcy (clasp with lanyard supporting supply tubes to ease pressure on ears); U.S. Pat. No. 5,025,805, issued Jun. 25, 1991 to Nutter (cylindrical soft sponge cuff around supply tubes to ease pressure and prevent skin injuries); U.S. Pat. No. 5,046,491, issued Sep. 10, 1991 to Derrick (device for collecting gases exhaled from both nose and mouth); U.S. Pat. No. 5,335,659, issued Aug. 9, 1994 to Pologe (device for mounting optical sensor on nasal septum); U.S. Pat. No. 5,509,409, issued Apr. 23, 1996 to Weatherholt (nasal cannula with face guards); U.S. Pat. No. 5,572,994, issued Nov. 12, 1996 to Smith (rotatable coupling in supply tubing); U.S. Pat. No. 5,636,630, issued Jun. 10, 1997 to Miller et al. (support for supply tubes); U.S. Pat. No. 5,704,916, issued Jan. 6, 1998 to Byrd (novel head strap for nasal cannula); and U.S. Pat. No. 5,704,799, issued Apr. 21, 1998 to Nielsen (device with one-way flow through cannula and flow restrictor to equalize flow into two nose members).

None of the above inventions and patents, taken either singly or in combination, is seen to describe the instant invention as claimed. Thus a ventilation interface for sleep apnea therapy solving the aforementioned problems is desired.

SUMMARY OF THE INVENTION

The ventilation interface for sleep apnea therapy interfaces a ventilation device which provides positive airway pressure (either continuous, bilevel, or intermittent) with the patient's airways. The ventilation interface includes a pair of nasal inserts made from flexible, resilient silicone which are oval shaped in cross-section and slightly tapered from a base proximal the ventilation supply to the distal tip end. A bead flange is disposed about the exterior of each insert at the distal end of the insert. A bleed port for release of exhaled air is defined through a conical vent projecting normally to the path of the incoming air flow, and continues through a nipple extending to the exterior of the air conduit. In one embodiment, a pair of nasal inserts are integral with a nasal cannula body, with bleed ports axially aligned with each insert. In another embodiment, each insert is independently connected to a separate, thin-walled, flexible supply line.

Advantageously, the construction of the nasal inserts permits the ventilation interface to be retained in the patient's nares without requiring a harness, head strap, or other retaining device. The nasal inserts do not merely seal the base of the nostrils, but are inserted into the nostrils farther than nasal pillows, as far as the nasal mucosal membrane, and are retained by resilient expansion of the inserts, the flanges engaging notches in the nares, together with the pressure of incoming air, which forms a positive seal to prevent the leakage of air past the inserts. The nasal inserts are constructed according to specifications which permit the inserts to be relatively thin-walled, and are oval-shaped in cross-section to conform to the shape of the nostrils. This construction permits the nasal inserts to have a large internal diameter in order to pass a greater volume of air than nasal pillows or prongs, without significant narrowing of the air passages, thereby maintaining lateral pressure, and avoiding drying and burning of the patient's nasal passages, as well as supplying a sufficient number of air molecules at the desired pressure to keep the patient's airways patent. Consequently, the ventilation device is more comfortable for the patient to wear while sleeping than conventional positive airway pressure devices, but at the same time is more effective in treating the patient's apnea.

The bleed ports are specially designed to avoid the whistling noises commonly experienced with conventional nasal masks and nasal pillows. By projecting the vent structure into the air passage normal to the direction of the air flow from the supply tubes, incoming air must turn ninety degrees and exit through a long, restricted diameter bleed port to vent to the atmosphere, eliminating whistling noises to increase patient comfort. In the embodiment having a nasal cannula body, the bleed ports are axially aligned with the nasal inserts, providing $CO_2$ with a direct path to exit the cannula body. When the nasal inserts are attached to independent supply tubes, the bleed ports are at the base of the nostrils, providing essentially normal exhalation.

When the nasal inserts are directly connected to the supply tubes, the nasal inserts may be even more thin-walled than when attached to a cannula body, resulting in an even greater volume of air supplied through the cannula body, up to a 20% increase in volume. In this case the supply tubes may be similar to heat-shrink tubing, being made from a very thin-walled thermoplastic material that is lightweight and flexible so that the supply tubing may collapse when not in use, but will expand to a predetermined diameter under pressure applied by a ventilator.

Under some circumstances it may prove advantageous to insert a valve between the nasal inserts and the supply lines to control the flow of air through the inserts. The valve may serve as an alternative to the bleed ports, providing isolation between inhaled and exhaled air, or may be connected to an electrical or mechanical control device for BiPAP or Intermittent Mechanical Positive Pressure Ventilation. One valve which may be used includes a valve body having a gate with a rim attached to one wall by a hinge and disposed to pivot between an inspiratory position in which the rim extends transversely across the inside perimeter of the nasal insert, and an expiratory position in which the rim swings downward against a stop. A one-way diaphragm extends across the rim which only permits inspiratory air to pass through the diaphragm. An exit port is defined in a sidewall of the valve body opposite the hinge. A flexible, inflatable bladder depends from the rim and is attached to the sidewalls of the valve body below the exit port. During inspiration incoming air inflates the bladder and raises the rim against a stop positioned above the exit port, the bladder inflating against the exit port and blocking the passage of air through the exit port. On expiration, the pressure of expired air against the one-way diaphragm opens the valve, expired air leaving the valve body through the exit port.

The nasal inserts may also be used without a mechanical ventilation supply, or positive airway pressure, in certain applications. For example, a one-way expiratory diaphragm may be placed across the base of the nasal inserts. A one-way inspiratory diaphragm is disposed in the sidewall of the nasal insert adjacent the base, so that the inspiratory diaphragm is disposed below the bottom of the nostril when the nasal inserts are worn. The inspiratory diaphragm may include a removable filter which is retained against the diaphragm by an elastic mesh, spring clips, hooks, or other retainer means. The filter may be of the type used to filter out dust, pollen, bacteria, allergens, and other nasal irritants. Use of the nasal inserts fitted with the filter while sleeping may be of therapeutic value in the treatment of asthma and other respiratory ailments.

Accordingly, it is a principal object of the invention to provide a ventilation interface for sleep apnea therapy having nasal inserts which seal against the nares and do not require a harness, head strap, or other external devices to maintain pressure for retaining the inserts in or against the patient's nostrils.

It is another object of the invention to provide a ventilation device having nasal inserts made of flexible, resilient plastic with a bead flange for retaining the inserts in the nares, wherein the walls of the insert are thin-walled and maintain lateral pressure in the nares in order to provide a greater internal diameter for the delivery of a greater volume of air molecules at a constant delivery pressure and without forcing ventilation gases through restricted ports or passageways so that drying and burning of the patient's nasal airways is avoided while delivering a therapeutic volume of air to maintain the apneic patient's airways in a patent condition.

It is a further object of the invention to provide a ventilation interface for sleep apnea therapy with equipped with a valve disposed between the nasal inserts and the source of positive airway pressure for controlling the flow of air through the nasal inserts.

Still another object of the invention is to provide a ventilation interface equipped with a removable filter for filtering allergens from inspired air in order to prevent asthmatic and allergic attacks.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 2B is a perspective view of a ventilation interface embodied in a nasal cannula body according to the present invention.

Similar reference characters denote corresponding features consistently throughout the attached drawings.

DETAILED DESCRIPTION OF THE PREFERRED EMBODIMENTS

Figure 1:
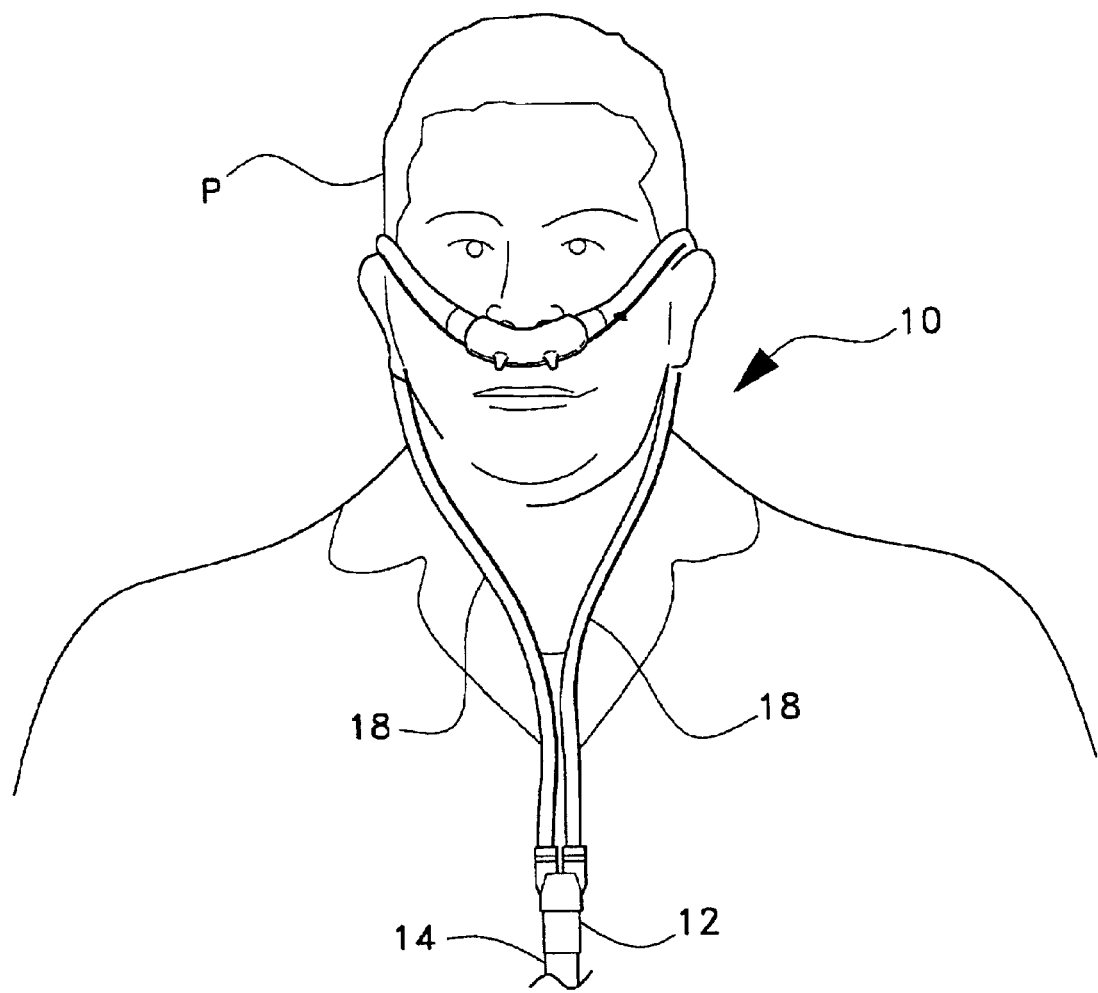
FIG. 1 is a front environmental view of a ventilation interface for sleep apnea therapy according to the present invention.
Figure 2A:
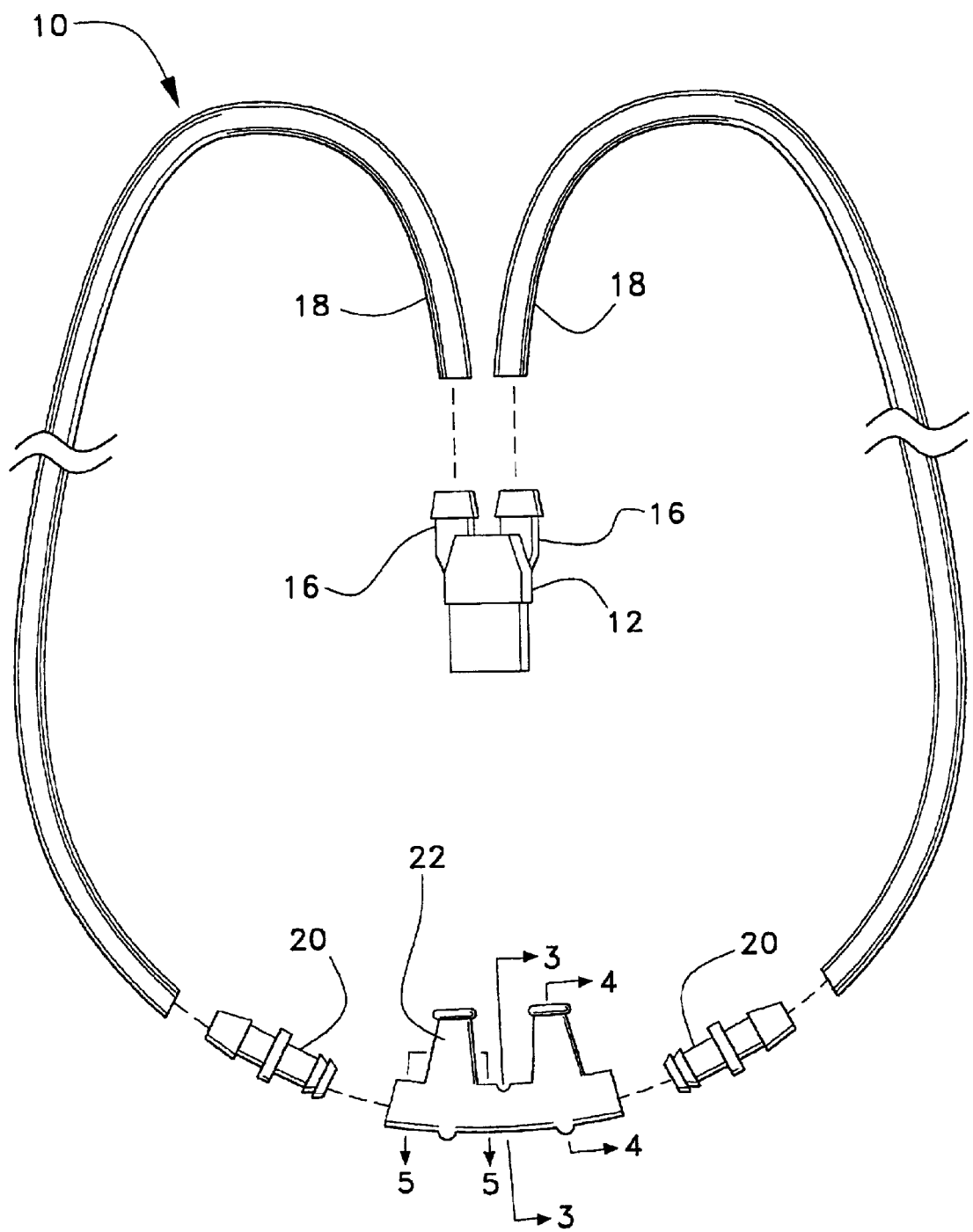
FIG. 2A is an exploded elevational of a ventilation interface according to the present invention.

The present invention is a ventilation interface for sleep apnea therapy, designated generally as 10 in the drawings. The ventilation interface 10 provides an interface for connecting a ventilation device which provides positive airway pressure (either continuous, bilevel, or intermittent) with the patient's airways. As shown in FIGS. 1 and 2A, the ventilation interface 10 includes a conventional adapter or Y-connector 12 having a first end adapted to receive a supply hose 14 from a mechanical ventilator (not shown) and a second end having a pair of ports 16 with barbed connectors for attachment to two supply tubes 18. Supply tubes 18 may be, e.g., 0.3125" ID (inside diameter) flexchem tubing, made of polyvinyl chloride or other conventional gas supply tubing. For sleep apnea therapy, the mechanical ventilator will usually supply room air at a pressure of between five and fifteen centimeters of water. The room air may be supplemented with oxygen if desired by splicing an oxygen supply line into supply hose 14 or using a triple port connector in lieu of Y-connector 12. It is normally unnecessary to humidify or add moisture to the air supplied by the mechanical ventilator in using the ventilation interface 10 of the present invention, as the interface 10 is designed to avoid stripping moisture from the nares, so that moisture does not have to be added to relieve patient discomfort from drying or burning sensation in the nasal airways.

In the embodiment shown in FIGS. 1 and 2A, the ends of the supply tubes distal from the Y-connector 12 are attached to opposite ends of a nasal cannula body 22 by barbed connectors 20. Barbed connectors 20 preferably have an inside diameter substantially equal to the inside diameter of supply tubes 18 in order to prevent any constriction or narrowing of the air passage which may cause increased velocity in air flow. Nasal cannula body 22, described more fully below, has a pair of nasal inserts 30 which are inserted into the nares of the patient P. The supply tubes may be looped over the patient's ears and joined to the Y-connector 12, which may be suspended at about the patient's chest level when the patient is standing, as shown in FIG. 1. For Bilevel Positive Airway Pressure (BiPAP) or Intermittent Mechanical Positive Pressure Ventilation therapy, a suitable valve may be connected between the supply tubes 18 and the cannula body 22. An exemplary valve is described in the Applicant's prior application, Ser. No. 09/524,371, filed Mar. 13, 2000, which is hereby incorporated by reference in its entirety.

The nasal cannula body 22 is shown in greater detail in FIG. 2B. The cannula body 22 is an arcuate, hollow, body having substantially flat top wall 22a and flat sidewalls 22b merging with a semi-cylindrical bottom wall 22c defining an air chamber 22d (seen more clearly in FIG. 3) for the passage of air and other gases, and having cylindrical tubes 24 at opposite ends which receive one end of the barbed connectors 20. A notch 26 is defined transversely across the top wall 22a of the cannula body 22, defining a pair of mounting pads 28. A pair of nasal inserts 30 are formed integral with the mounting pads 28. The nasal inserts 30 are hollow and form a continuous flow path or conduit for the passage of inhaled and exhaled gases between the patient's nasal air passages and the air chamber 22d.

Figure 3:
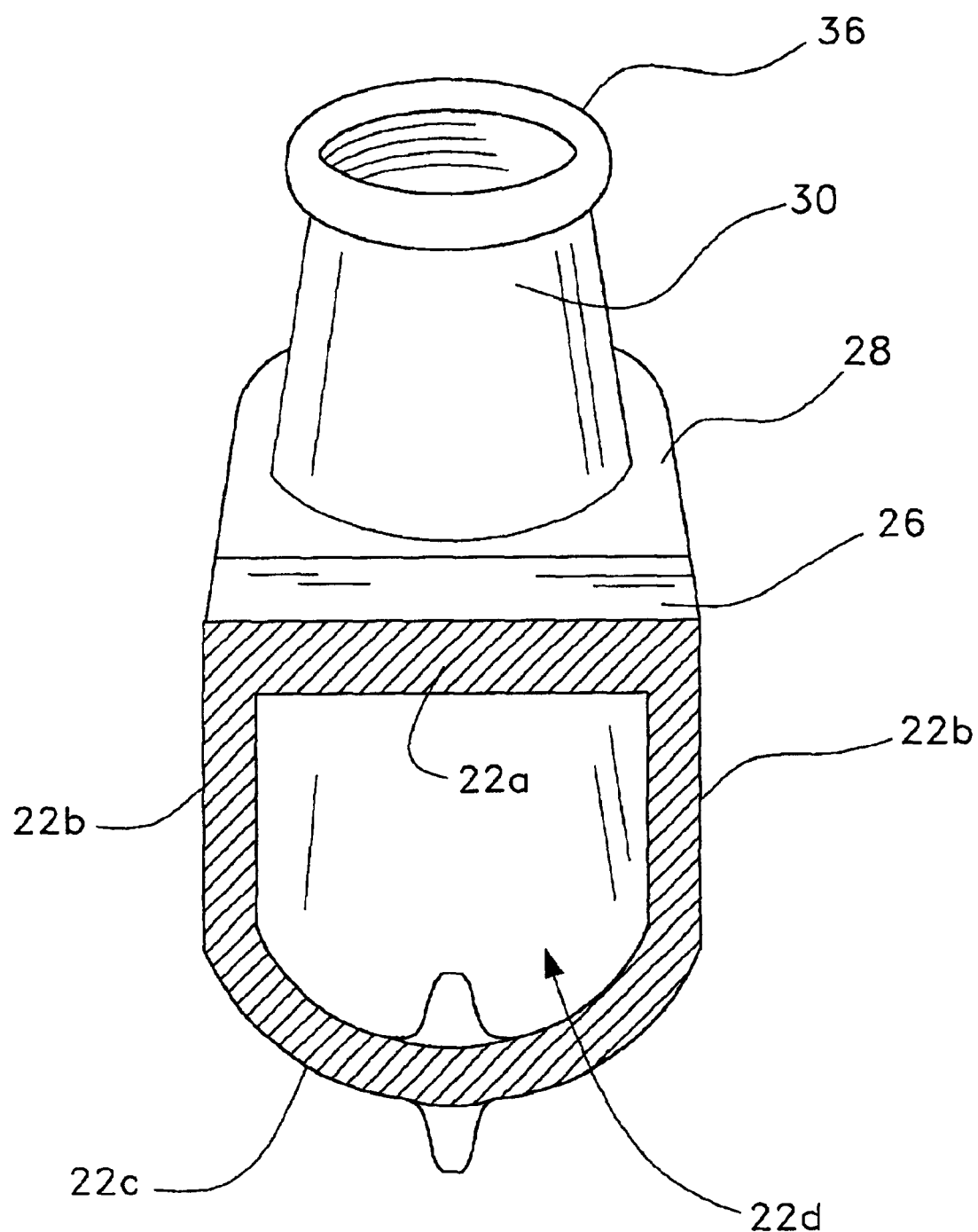
FIG. 3 is a section view along the lines 3—3 of FIG. 2A.
Figure 4:
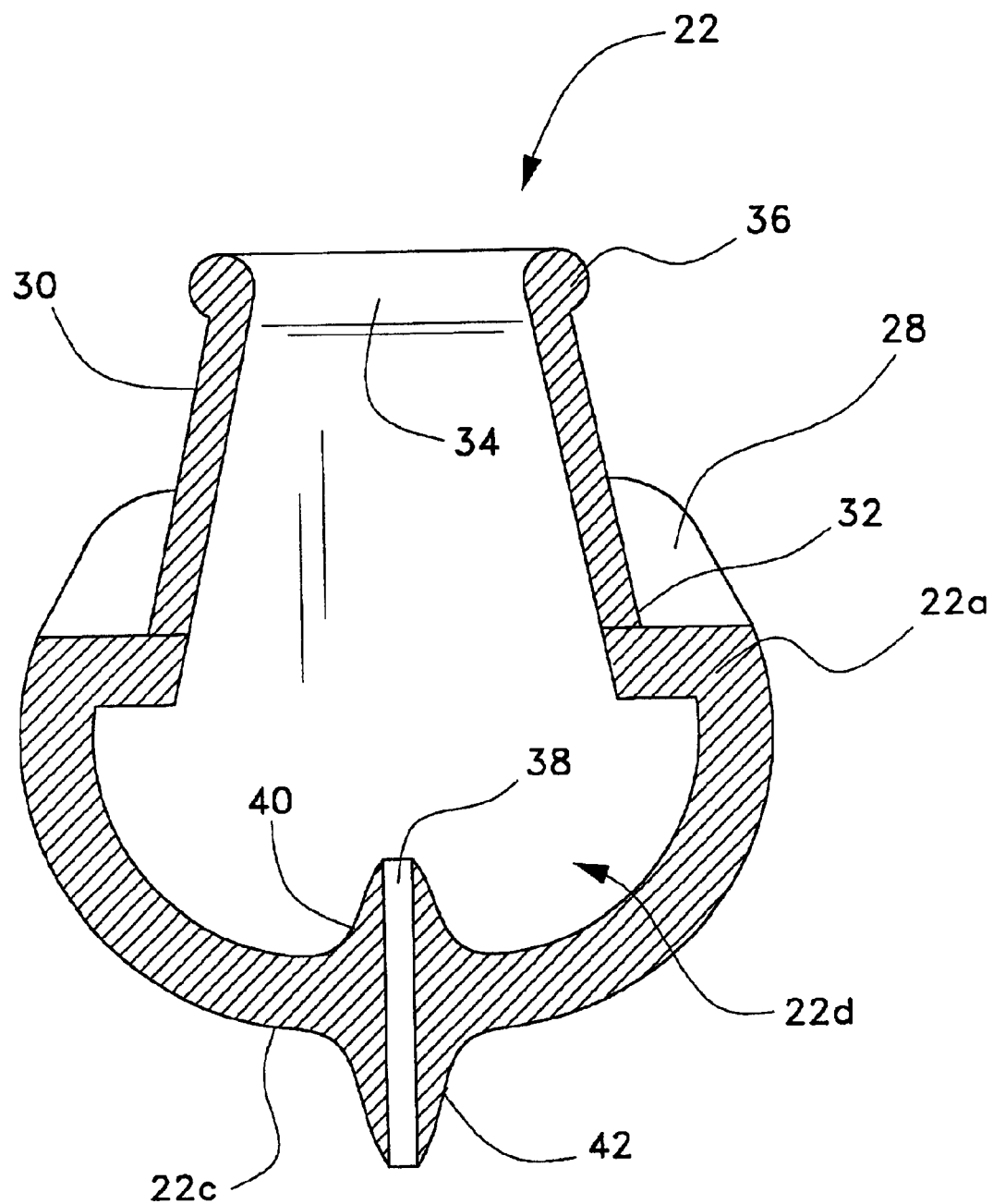
FIG. 4 is a section view along the lines 4—4 of FIG. 2A.
Figure 5:
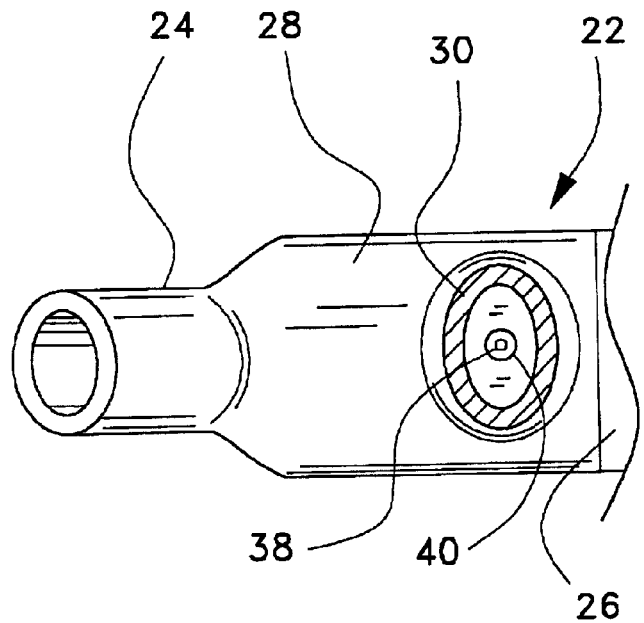
FIG. 5 is a section view along the lines 5—5 of FIG. 2A.

The nasal inserts are shown in greater detail in FIGS. 3, 4, and 5. The nasal inserts 30 are substantially oval in cross-section, with the major axis substantially parallel with the notch and the minor axis normal to the notch. The nasal inserts 30 taper slightly from a wide base 32 proximal the cannula body 22 to the open distal tip ends 34. The nasal inserts 30 have a flange 36 about the distal tip ends 34 on the exterior surface of the inserts 30, which may be formed as a semi-cylindrical bead.

The cannula body 22, including the nasal inserts 30, are preferably made from silicone elastomer. The cannula body 22 or air chamber 22d has an internal diameter of at least 0.3125 inches throughout its length. The walls of the nasal inserts 30 may be thinner than the top wall 22a. The thickness of the walls of the nasal inserts 30 are preferably between about $1/32$ and $1/20$ inches. The thickness of the walls at the flange 36 may be about $1/16$ inches. The hardness of the walls of the nasal insert 30, as tested on a type A Shore durometer, may range between about 15 and 40, preferably about 30. If the walls of the nasal inserts 30 are made any thinner, they will fail to have sufficient integrity, and if made any thicker, they will have insufficient flexibility to form a seal against the nares. The thinness and softness of the nasal inserts 30 make them virtually unnoticeable while in the nostrils. For an adult patient, the nasal inserts may have a height of between about 0.25 and 0.75 inches. The internal diameter of the nasal inserts 30 may measure about 0.75" on the major axis and 0.5" on the minor axis, allowing for generous laminar air flow and delivering pressure more by volume of air molecules than velocity of air flow, and deliver about double the volume of nasal pillows, which have a round internal diameter of, for example, about 0.25 inches. Nasal pillows cannot be made with such large internal diameters, because it becomes difficult to create a seal under the bottom of the nose, as the pillows would have an internal diameter larger than the internal diameter of the nares, and the pillows are not as flexible as the nasal inserts 30 of the present invention.

In use, the nasal inserts 30 are inserted up the patient's nostrils until the flanges 36 lodge against the mucous membranes. As such, the nasal inserts 30 are considered an invasive device. Testing has confirmed that the nasal inserts 30 are biocompatible and meet regulatory requirements. The nasal inserts are retained in the patient's nares by the flanges 36, by the flexibility and resiliency of the silicone elastomer, and by lateral pressure of the room air, which is maintained at between five and fifteen centimeters of water. The oval cross-section of the nasal inserts 30 is shaped to conform to the normally oval shape of the nares. The relative large internal diameter of the nasal inserts 30 permits air to be supplied to the patient's airways in sufficient volume at the driving pressure without accelerating the rate of airflow that the patient has sufficient positive airway pressure to be of therapeutic value in maintaining the patient's airways patent during an episode of obstructive apnea without drying the nasal passages. The notch 26 in the top wall 22a of the cannula body 22 lends additional flexibility to the cannula body 22, so that the nasal cannula 22 can be adjusted for deviated septums, thick septums, and other anatomical variations in the configuration of the nostrils.

The cannula body 22 has a pair of bleeder ports 38 disposed in the bottom wall 22c directly below and axially aligned with the nasal inserts 30. The bleeder ports are formed by an upper conically shaped nipple 40 extending upward into the air chamber 22d, and a lower conically shaped nipple 42 extending below the bottom wall 22c. The bleeder port has an internal diameter if about three millimeters and extends for a length of about 0.25 inches. The upper nipple 40 extends about 0.125 inches into the air chamber 22d. The internal diameter of the bleeder port 38 is ample to permit venting of carbon dioxide exhaled by the patient while not being so large as to cause a significant pressure drop in the cannula body 22, and axial alignment of the bleeder port 38 with the nasal inserts 22 creates a direct path for venting of the expired gases. At the same time, laminar flow of air supplied by the supply tubes is normal to the bleeder ports 38, so that air supplied by the ventilator must bend ninety degrees to exit through the elongated bleeder port 38. The effect of this construction is that the bleeder port 38 is virtually silent in operation, eliminating the whistle associated with bleeder holes in conventional ventilation interfaces.

Figure 6:
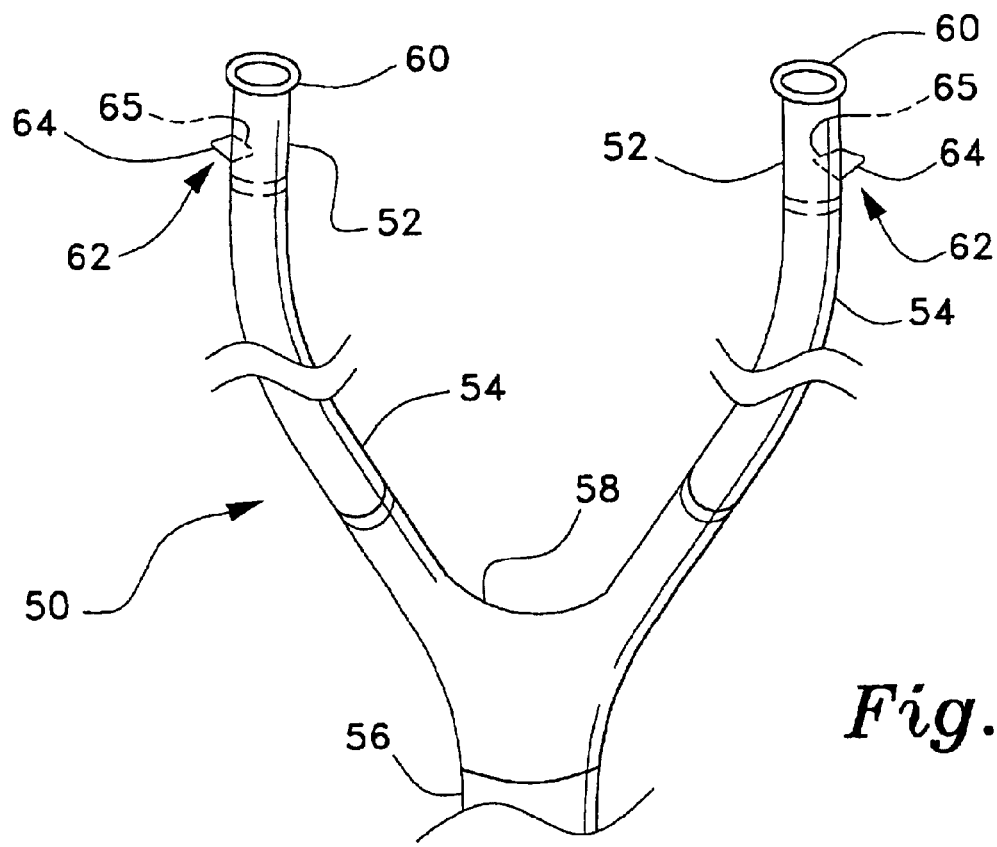
FIG. 6 is a perspective view of an embodiment of the ventilation interface with the nasal inserts incorporated into independent supply tubes.

FIG. 6 is a generally diagrammatic view of an alternative embodiment of the ventilation interface, designated 50 in the drawing. In this embodiment, each nasal insert 52 is connected to a separate supply tube 54, the supply tubes 54 being connected to the mechanical ventilator supply hose 56 by a suitable Y-connector 58 or adapter, the cannula body 22 and common air chamber 22d being omitted. The nasal inserts 52 have substantially the same construction as nasal inserts 30, being oval in cross-section and having a similar height and an annular flange 60 about the distal tip for lodging the nasal insert 52 in a naris. The nasal insert 52 is also made from silicone elastomer, and has the same softness, thickness, flexibility and resilience as the nasal insert 30. In this configuration, since the inserts are not connected to the cannula body 22, the angle at which the inserts 52 enter the nostrils is not restricted by the cannula body 22, and therefore the nares can accept a greater displacement, and may accommodate a 20% greater volume of air molecules through the insert 52 than the insert 30.

In this embodiment, the supply tubes 54 may be made from a flexible, lightweight, but relatively inelastic thermoplastic material, similar to heat shrink tubing, so that the supply tubes 54 may be at least partially collapsed in the absence of pressure from the mechanical ventilator, but expand to their maximum diameter under a pressure of between five to fifteen centimeters of water. The lightweight of the supply tubes 54 decreases any pressure on the patient's ears resulting from the weight of the supply tubes, increasing patient comfort. The bleeder ports 62 have a similar construction to the bleeder ports 38, having an internal nipple 65 normal to the axis of the nasal insert 52 and an external nipple 64, the bleeder ports 62 being just above the base of the inserts 52 and normal to the flow of supply air through the inserts 52.

It will be understood by those skilled in the art that the dimensions of the nasal inserts 30 and 52, and of the bleeder ports 38 and 62, are representative dimensions for a ventilation interface 10 or 50 designed for adults, and that the ventilation interface 10 or 50 may be made with correspondingly reduced dimensions for teenage children, preteens, and infants. It will also be understood that the nasal inserts 30 and 52 may be made from thermoplastic elastomers other than silicone, providing that the material has similar softness, resilience, flexibility, and biocompatibility. It will also be understood by those skilled in the art that the nasal inserts 30 and 52, although illustrated in conjunction with ventilation devices for the treatment of sleep apnea, may be used in any other application where it is desirable to have an interface forming a seal between a person's nasal airways and a ventilation or gas collection device, including, but not limited to, rescue breathing apparatus used by firefighters and other emergency personnel, scuba diving tanks, etc.

Figure 7:
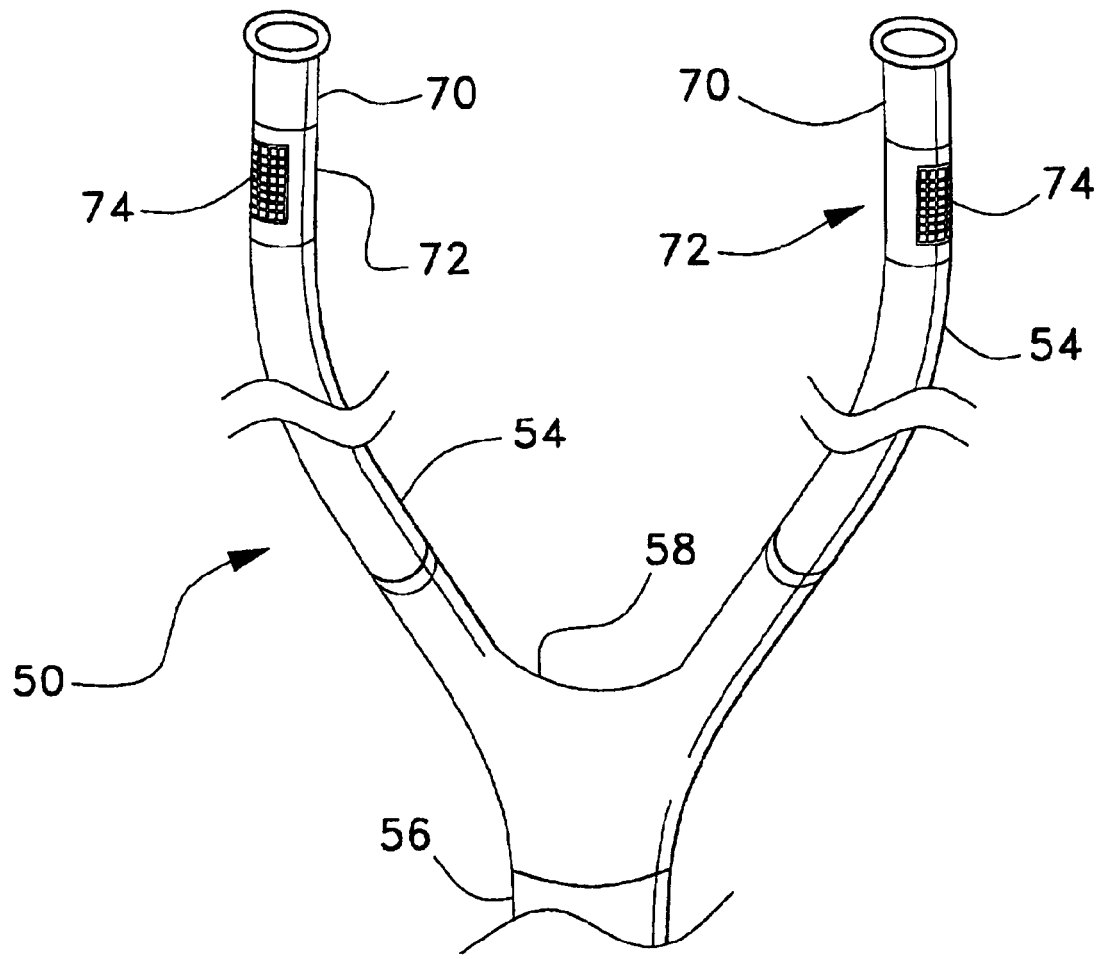
FIG. 7 is a perspective view of an embodiment of the ventilation interface with the nasal inserts incorporated into independent supply tubes, and having valves disposed between the nasal inserts and supply tubes.
Figure 8:
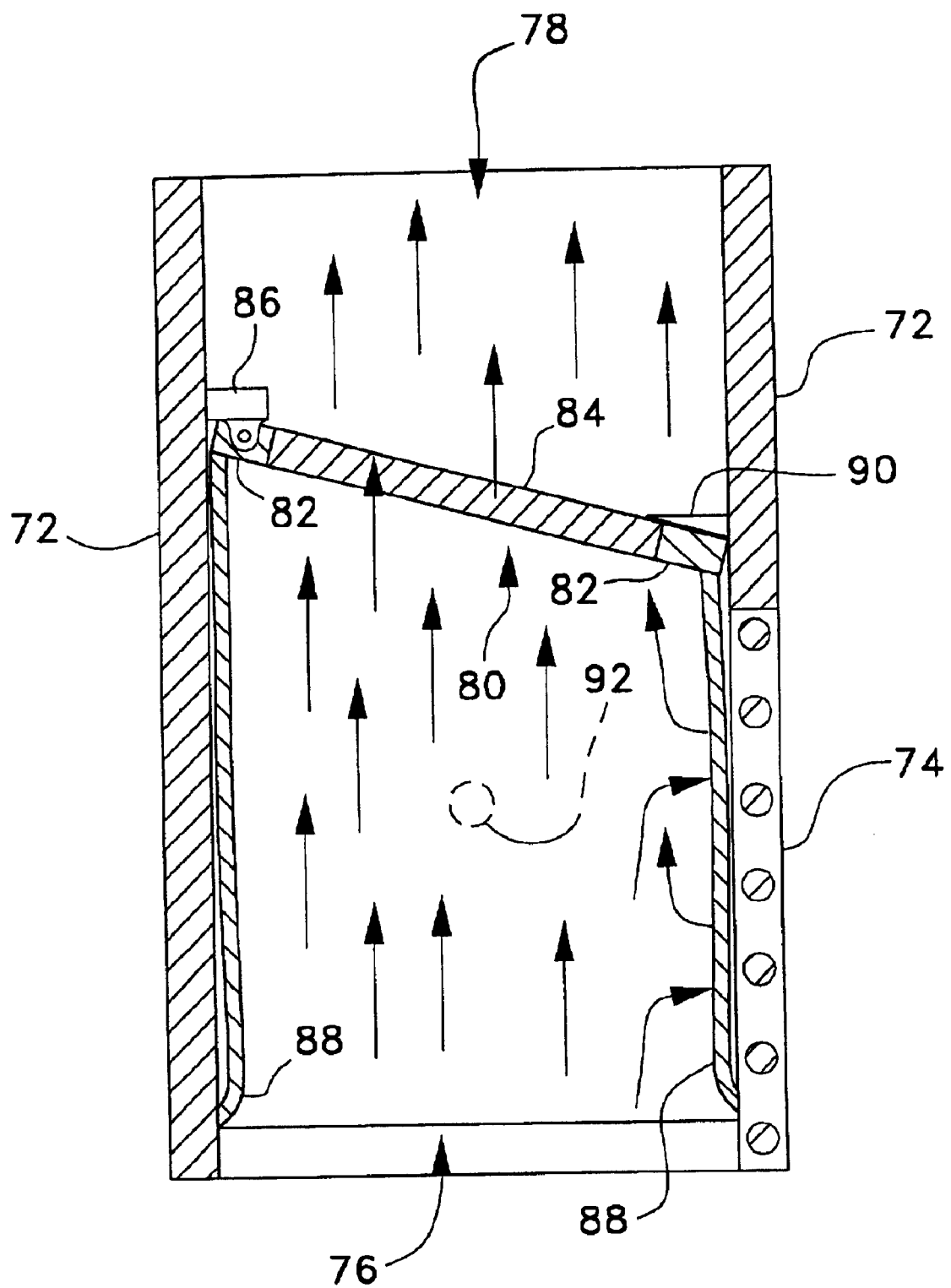
FIG. 8 is a longitudinal sectional view through the valve assembly of FIG. 7 showing the position of the valve during the inspiratory cycle.
Figure 9:
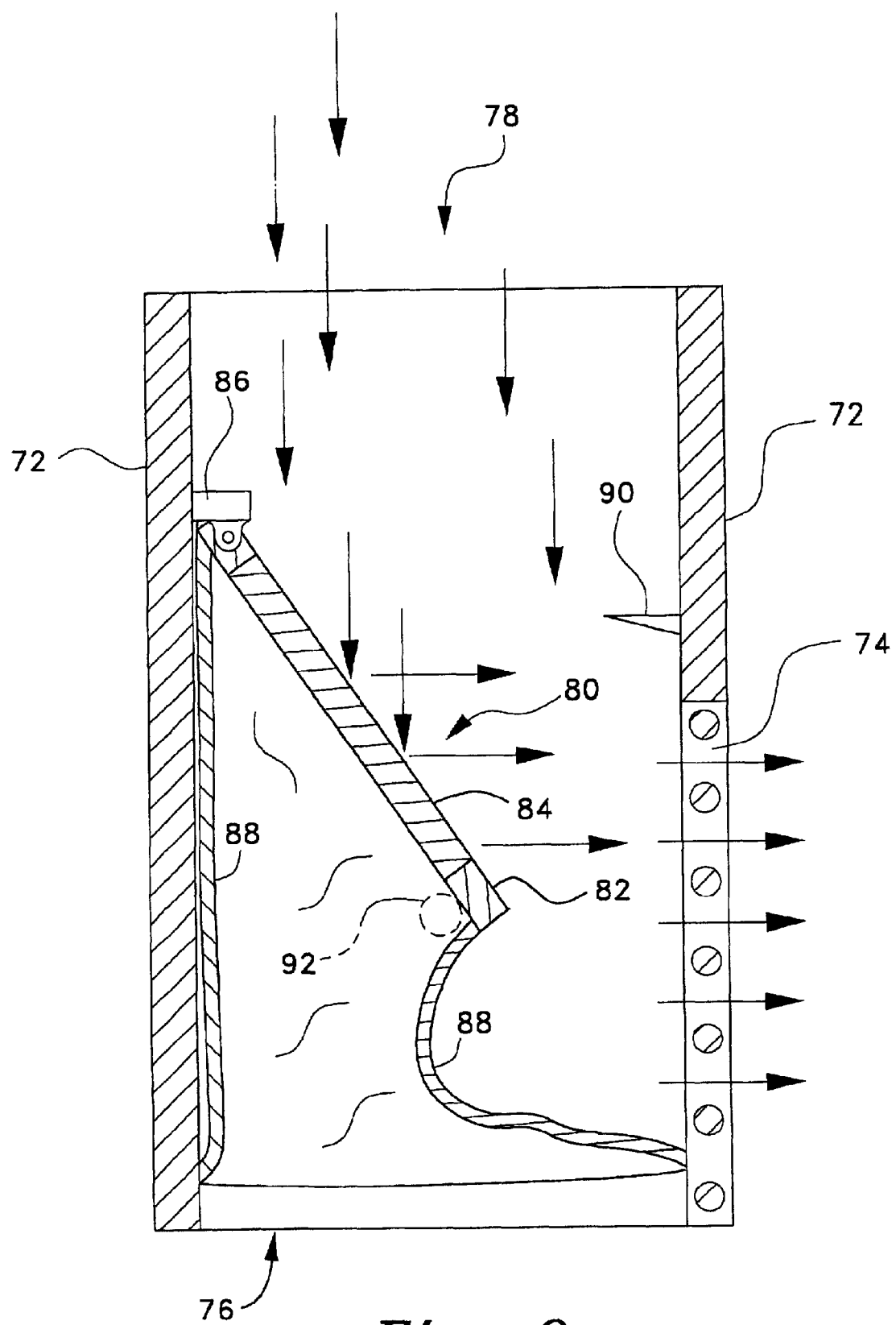
FIG. 9 is a longitudinal sectional view through the valve assembly of FIG. 7 showing the position of the valve during the expiratory cycle.

In lieu of bleeder ports, the ventilation interface may use a valve for providing an exit port for exhaled air, and for providing isolation between inhaled and exhaled air. FIGS. 7–9 show the apparatus of FIG. 6 modified by a flapper type valve inserted inline between the nasal inserts 70 and the supply tubes 54. The valve includes a valve body 72 having an exit port 74 defined by a mesh grid in a sidewall of the valve body 74. In FIG. 7 the components shown below the valve body 72 are identical to those shown in FIG. 6, and will not be described further. Nasal inserts 70 are identical in construction to inserts 30 and 52, and will not be described further. Valve body 72 may be constructed from the same material as nasal inserts 70. Although shown as generally oval in cross-section in FIGS. 7–9, the shape of the valve body is not critical and it will be understood that the valve body 72 may have any suitable shape in transverse cross-section, including oval, circular, square, etc.

FIG. 8 is a sectional view showing the position of the valve components during the inspiratory cycle. The valve body 72 is hollow and defines an air conduit extending between its inferior end 76 and superior end 78. Disposed within the valve body 72 is a flapper type disk or gate 80, having a relatively rigid rim 82 defining the perimeter of the gate 80, and a one-way diaphragm 84 stretched across and supported by the rim 82. The perimeter of the rim 82 is slightly smaller than the inside perimeter of the valve body 72 so that the gate 80 closes the air conduit when disposed in the position shown in FIG. 8. The one-way diaphragm 84 permits air from the supply tubes 54 to pass through the diaphragm in the direction shown by the arrows in FIG. 8, but does not permit expired air to travel through the diaphragm 84 in the opposite direction. The gate 80 is pivotally attached to a sidewall of the valve body 72 by a hinge 86. A flexible, inflatable/deflatable tubular bladder 88 extends between the inferior end 76 of the valve body 72 and the rim 82 of the gate 80. The bladder 88 is open at the inferior end of the valve body 72 and is closed by the rim 82 and diaphragm 84 at the opposite end of the bladder 88.

During inspiration, inspired air travels from the supply tubes 54 and enters the valve body 72 at the inferior end 76. The inspired air inflates the bladder 88, causing the rim 82 of the gate 80 to pivot upward against a stop 90 disposed on a sidewall of the valve body 72 which limits travel of the gate 80. The stop 90 may be a post or protrusion extending into the hollow valve body 72, or the stop 90 may be an internal flange disposed about the entire inner circumference of the valve body 72 which defines a valve seat and which forms a seal with the rim 82 during inspiration. As shown in FIG. 8, the bladder 88 inflates against the exit port 74, sealing the exit port 74 so that air does not escape through the exit port 74 during inspiration. Inspired air continues through the one-way diaphragm 84 and exits the superior end of the valve body 72, thence passing through the nasal inserts 70 and into the patient's nasal air passages.

FIG. 9 shows the position of the valve during expiration. The patient exhales air through the nasal inserts 70 and the air enters the superior end of the valve body 72. The pressure of the expired air against the one-way diaphragm causes the gate 80 to pivot on the hinge 86 until the rim 82 engages a stop post 92 disposed on a sidewall of the valve body 72, which limits downward travel of the gate 80. The flexible bladder 88 is drawn down by the rim 82, uncovering the exit port 74. Expired air is then released to the atmosphere through the exit port 74, as shown by the direction of the arrows in FIG. 9.

The flexible bladder 88 may be made from a thin layer of biocompatible, gas impermeable material, e.g., latex. The rim 82 of the gate 80 may be made from any rigid plastic material. The one-way diaphragm 84 may be any one-way gas permeable membrane. Such membranes are well-known in the medical arts.

Figure 10:
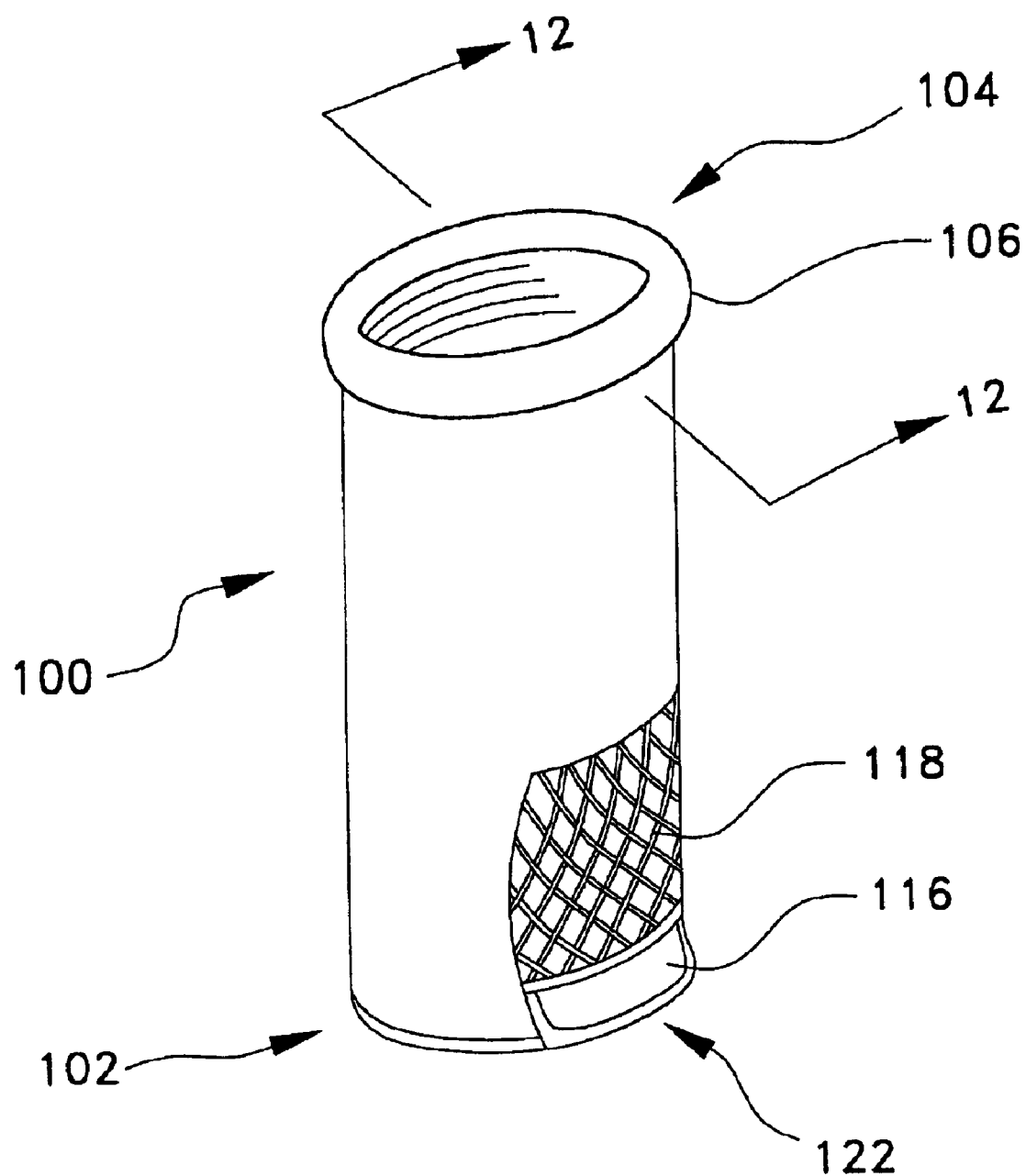
FIG. 10 is a front perspective view of a left nostril nasal insert fitted with a filter for therapeutic treatment of asthma and other respiratory ailments, the right nostril nasal insert being a mirror image.
Figure 11:
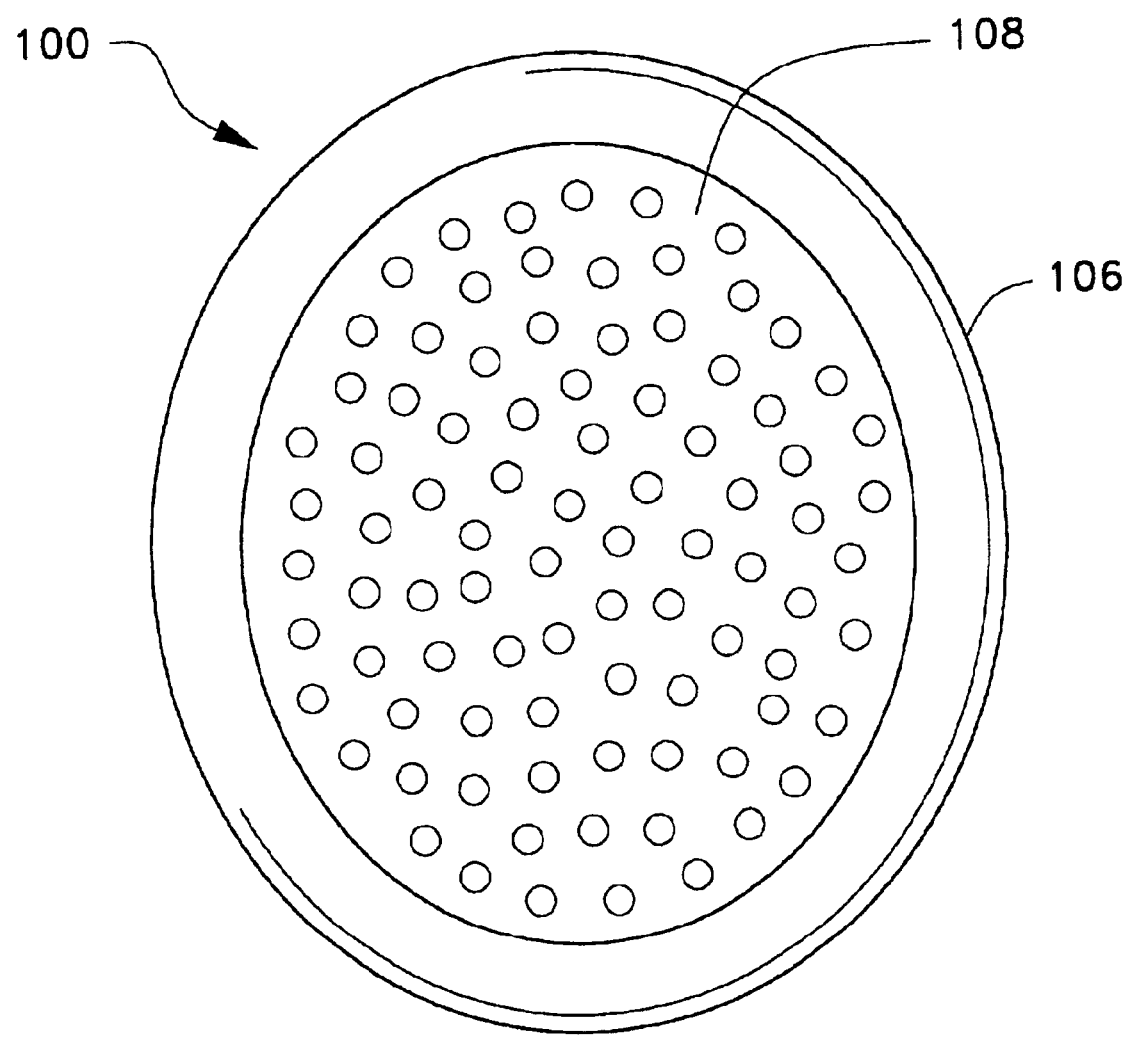
FIG. 11 is a top view of the nasal insert of FIG. 10.
Figure 12:
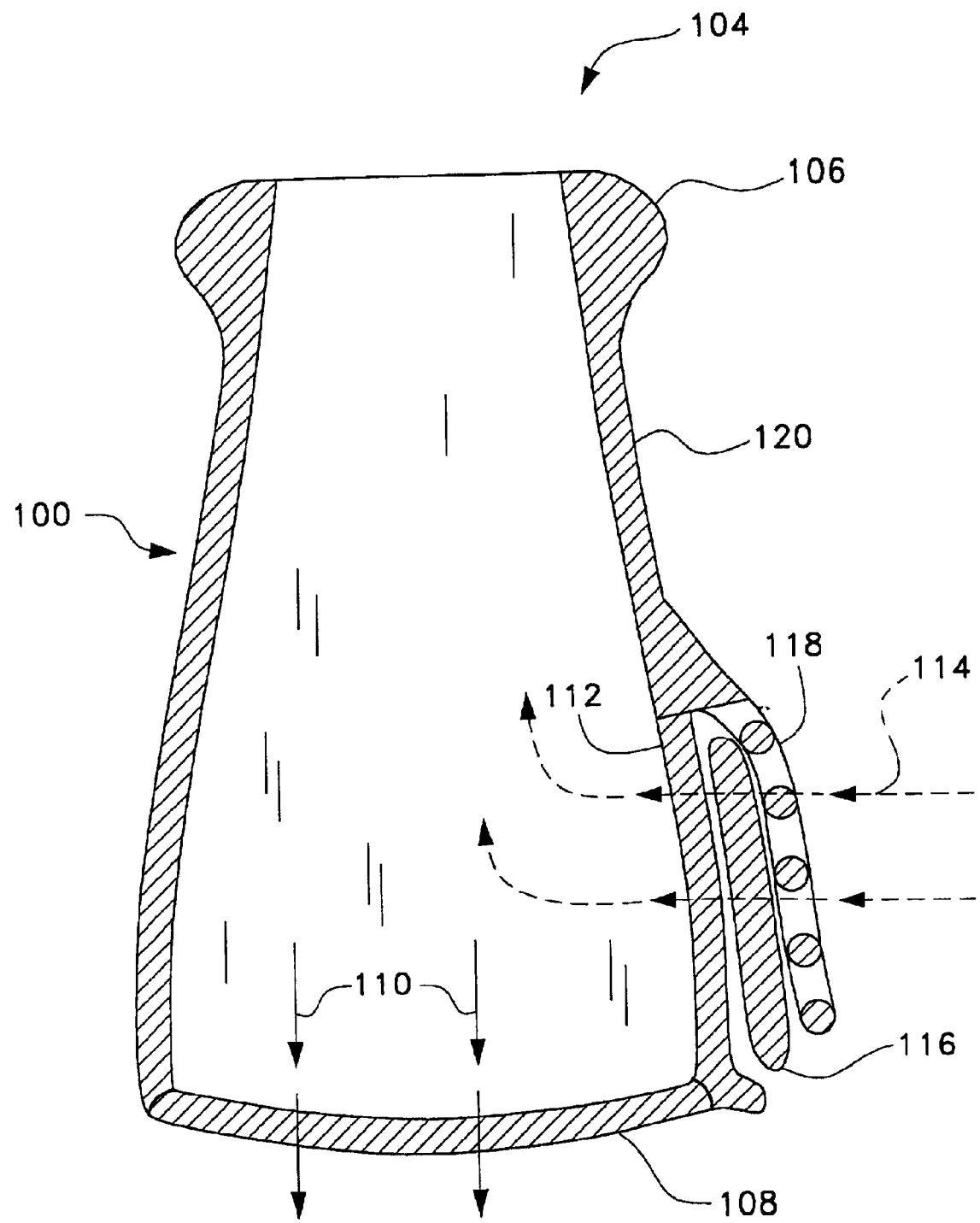
FIG. 12 is a section view along the lines 10—10 of FIG. 12.

The nasal inserts may also be used without being connected to a source of positive airway pressure. FIGS. 10–12 show an embodiment of the nasal inserts fitted with a filter that may be used for the treatment and prevention of asthmatic attacks and other respiratory impairments. A front view of a nasal insert adapted for the left nostril is shown in FIG. 10, the nasal insert for the right nostril being a mirror image. The nasal insert 100 has substantially the same construction as the nasal inserts 30, 52, and 70, i.e., the nasal inserts 100 are substantially oval in cross-section, tapering slightly from a wide base 102 to the tip end 104. The nasal insert 100 has a flange 106 about the tip end 104 on the exterior surface of the insert 100, which may be formed as a semi-cylindrical bead.

The nasal insert 100 is preferably made from silicone elastomer. The thickness of the walls of the nasal insert 100 is preferably between about $\frac{1}{32}$ and $\frac{1}{20}$ inches. The thickness of the wall at the flange 106 may be about $\frac{1}{16}$ inches. The hardness of the wall of the nasal insert 100, as tested on a type A Shore durometer, may range between about 15 and 40, preferably about 30. The thinness and softness of the nasal insert 100 makes the insert virtually unnoticeable while in the nostrils. For an adult patient, the nasal insert 100 may have a height of between about 0.25 and 0.75 inches. The internal diameter of the nasal insert 100 may measure about 0.75" on the major axis and 0.5" on the minor axis, allowing for generous laminar air flow.

As shown in FIGS. 10–12, the nasal insert 100 has a one-way expiratory diaphragm 108 disposed across the base 102 of the insert and is adapted for receiving a filter insert in the sidewall which is disposed laterally in the insert 100. The one-way expiratory diaphragm 108 is positioned directly below the patient's naris, and permits the flow of exhaled air through the diaphragm 108 in the direction shown by the solid arrows 110 in FIG. 12, but does not permit air flow through the diaphragm in the opposite direction.

The nasal insert includes a one-way inspiratory diaphragm 112 disposed laterally in the sidewall of the insert 100. The inspiratory diaphragm 112 permits the flow of air into the insert 100 in the direction shown by the dashed arrows 114 in FIG. 12, but not in the opposite direction. The inserts 100 include a removable, disposable, replaceable filter 116 and means for maintaining the filter 116 in the sidewall of the insert 100. FIG. 12 shows an elastic mesh 118, the elastic mesh 118, one-way diaphragm 112 and sidewall 120 defining an envelope for retaining the filter 116, the mesh 118 and diaphragm defining a slot 122. The filter 116 may be inserted through the slot 122 where it is retained against the one-way diaphragm 112 by the elastic mesh 118, and may be removed by using a fingernail, toothpick, nail file, or other device for pulling the filter 116 out of the envelope. Other devices may be used to retain the filter 116 against the one-way diaphragm 112 if desired, e.g., spring clips, hooks, etc.

The filter 116 filters out any particles that may cause allergies or asthmatic attacks, such as dust, pollen, allergens, and bacteria from inspired air. Such filters are well known in the medical arts, and will not be described further.

It is to be understood that the present invention is not limited to the embodiments described above, but encompasses any and all embodiments within the scope of the following claims.

I claim:

1. A ventilation interface, comprising:
   (a) a pair of nasal inserts, each nasal insert being a hollow body made from a flexible, resilient, soft biocompatible material, each nasal insert having a base end adapted for connection to a ventilator air flow and an open distal tip end, each nasal insert being substantially oval in cross-section at the base end and the distal end and continuously oval in cross-section between the base end and the distal end;
   (b) a flange formed as a bead disposed about the distal tip end of each said nasal insert, the flange being adapted for forming a seal against a naris of a patient's nose;
   (c) wherein each said nasal insert is capable of being compressed and inserted into the patient's naris to a patient's mucosal membrane and being retained therein solely by said flange, by the resilience of said nasal insert, and by lateral pressure against the naris from ventilator air flow; through each said nasal insert; and
   a pair of valves, each of the valves including a hollow valve body defined by at least one sidewall and having a superior end and an inferior end, the base of each said nasal insert being attached to the superior end of one of said valve bodies, respectively, in order to form a continuous air conduit.

2. The ventilation interface according to claim 1, further comprising a pair of supply tubes for delivering a gas from a ventilator, the inferior end of each of said valve bodies being connected to a separate one of the pair of supply tubes so that each said nasal insert is independently supplied with gas from the ventilator.

3. The ventilation interface according to claim 1, wherein each said valve further comprises:
   (a) an exit port defined in said at least one sidewall, the exit port being formed by a mesh grid;
   (b) a hinge attached to said at least one sidewall opposite said exit port;
   (c) a gate pivotally attached to said hinge, the gate having a rigid rim defining the perimeter of the gate and a one-way, gas permeable diaphragm extending across the rim; and
   (d) a flexible, tubular bladder having a first end attached to the rim of said gate and an open second end attached to the side wall of said valve body;
   wherein said gate pivots between a first position during inspiration in which the rim of said gate is above said exit port, said bladder inflating to form a seal over said exit port, and a second position during expiration in which the rim of said gate is below said exit port, opening said exit port for release of exhaled air to the atmosphere.

4. The ventilation interface according to claim 3, wherein said one-way diaphragm permits inflow of inspired air from the inferior end of said valve body through said diaphragm and the superior end of said valve body, but blocks outflow of exhaled air in a direction opposite to inflow.

5. The ventilation interface according to claim 3, wherein each said valve further comprises a stop extending from the sidewall of said valve body positioned above said exit port in order to limit travel of said gate during inspiration.

6. The ventilation interface according to claim 3, wherein each said valve further comprises a stop post extending from the sidewall of said valve body positioned below said exit port in order to limit travel of said gate during expiration.

7. A ventilation interface, comprising:
   (a) a nasal insert, the nasal insert being a hollow body made from a flexible, resilient, soft, biocompatible material, having a base end and a tip end, the nasal insert being substantially oval in cross-section at the base end and the tip end and continuously oval in cross-section between the base end and the tip end;
   (b) a flange formed as a bead disposed about the tip end of said nasal insert, the flange being adapted for forming a seal against a naris of a patient's nose; and
   (c) a valve having a hollow valve body including a superior end attached to the base end of said nasal insert and an inferior end adapted for attachment to supply tubing from a ventilator, the valve having:
      (i) an exit port defined in said valve body;
      (ii) a gate pivotally attached to said valve body, the gate having a rigid rim and a one-way gas permeable diaphragm extending across the rim; and
      (iii) a flexible, tubular bladder having a first end, attached to the rim of said gate and an open second end attached to said valve body;
   (d) wherein said nasal insert is capable of being compressed and inserted into the patient's naris to a patient's mucosal membrane and being retained therein solely by said flange and by the resilience of said nasal insert; and
   (e) wherein said gate pivots between a first position during inspiration in which the rim of said gate is above said exit port, said bladder inflating to form a seal over said exit port, and a second position during expiration in which the rim of said gate is below said exit port, opening exit port for release of exhaled air to the atmosphere.

8. The ventilation interface according to claim 7, wherein said one-way diaphragm permits inflow of inspired air from they inferior end of said valve body through said diaphragm and the superior end of said valve body, but blocks outflow of exhaled air in a direction opposite to inflow.

9. The ventilation interface according to claim 7, wherein said valve further comprises a stop extending from said valve body, positioned above said exit port in order to limit travel of said gate during inspiration.

10. The ventilation interface according to claim 7, wherein said valve further comprises a stop post extending from said valve body positioned below said exit port in order to limit travel of said gate during expiration.

11. A ventilation interface, comprising:
   (a) a nasal insert, the nasal insert being a hollow body made from a flexible, resilient, soft, biocompatible material, having a base end and a tip end, the nasal insert being substantially oval in cross-section at the base end and the tip end and continuously oval in cross-section between the base end and the tip end;
   (b) a flange formed as a bead disposed about the tip end of said nasal insert, the flange being adapted for forming a seal against a naris of a patient's-nose;

(c) a one-way expiratory diaphragm disposed across the base end of said nasal insert, the expiratory diaphragm permitting passage of exhaled air from the tip end through the base end, but preventing passage of inhaled air through the base end towards the tip end;

(d) a one-way inspiratory diaphragm disposed in said nasal insert adjacent the base end, the inspiratory diaphragm permitting passage of inhaled air from outside said nasal insert, through the inspiratory diaphragm, and into said nasal insert, but preventing passage of exhaled air through the inspiratory diaphragm and out of said nasal insert;

(e) a removable filter disposed over said inspiratory diaphragm; and (f) means for retaining said filter;

wherein said nasal insert is capable of being compressed and inserted into the patient's naris to a patient's mucosal membrane and being retained therein solely by said flange and by the resilience of said nasal insert, said inspiratory diaphragm being disposed below the patient's naris.

12. The ventilation interface according to claim 11, wherein said filter is capable of filtering at least one irritant selected from the group consisting of dust, pollen, allergens and bacteria from inhaled air.

13. The ventilation interface according to claim 11, wherein said retaining means comprises an elastic mesh disposed over said inspiratory diaphragm.

* * * * *